United States Patent
Robotti

(10) Patent No.: US 7,208,573 B2
(45) Date of Patent: Apr. 24, 2007

(54) ENRICHMENT OF PHOSPHATE PEPTIDES FOR PROTEOMIC ANALYSIS

(75) Inventor: Karla M. Robotti, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 444 days.

(21) Appl. No.: 10/698,106

(22) Filed: Oct. 31, 2003

(65) Prior Publication Data

US 2005/0095725 A1     May 5, 2005

(51) Int. Cl.
*C07K 1/36*     (2006.01)
(52) U.S. Cl. .................................................... 530/344
(58) Field of Classification Search .................... None
See application file for complete search history.

(56) References Cited

U.S. PATENT DOCUMENTS 5,679,773 A * 10/1997 Holmes ...................... 530/334

OTHER PUBLICATIONS

Zhou et al. "A systematic approach to the analysis of protein phosphorylation." Nat. Biotech. 2001, 19, 375-378.*

Fields et al. "Solid-phase peptide synthesis and solid-state NMR spectroscopy of [Ala-15N][Val]gramicidin A." Proc. Natl. Acad. Sci. USA 1988, 85, 1384-1388.*

Oda et al. "Enrichment analysis of phosphorylated proteins as a tool for probing the phosphoproteome." Nat. Biotech. 2001, 19, 379-382.*

Mercader et al. "Generation of anticalins with specificity for a nonsymmetric phthalic acid ester." Anal. Biochem. 2002, 308, 269-277.*

Kundu & Roy "Aminopropyl silica gel as a solid support for preparation of glycolipid immunoadsorbent and purification of antibodies." J. Lipid Res. 1979, 20, 825-833.*

* cited by examiner

*Primary Examiner*—Cecilia J. Tsang
*Assistant Examiner*—Christina M. Bradley

(57) ABSTRACT

The present invention is a method, and a kit for carrying out the method, of separating phosphorylated peptides from a mixture of phosphorylated and unphosphorylated peptides. The method involves reacting a collection of peptides, in which some of the peptides have one or more phosphate groups, with a first resin. The peptides are then reacted with a capture ligand which reacts with the phosphate group of the phosphorylated peptides to form a bond. The capture ligand is used to separate the phosphorylated peptides from the unphosphorylated peptides.

11 Claims, 4 Drawing Sheets

ENRICHMENT OF PHOSPHATE PEPTIDES FOR PROTEOMIC ANALYSIS

BACKGROUND

Sequencing of the human genome, and the genomes of other species, has emphasized the fact that the expression and properties of a protein are often dependent on posttranslational modifications and, thus, cannot be predicted from the DNA sequence. This realization has spurred an interest in proteomics, the study of protein expression within a cell under defined conditions.

Traditionally, proteins from biological samples have been isolated and identified by separating the proteins using 2-D gel electrophoresis followed by identification of the protein using mass spectrometry. However, this method is time consuming and can only detect proteins that are highly abundant in the biological sample. Severe streaking causes deterioration in resolution of the electrophoretic separation when high loading is used in an attempt to visualize less abundant proteins.

Particular difficulties have been encountered in attempts to use 2-D gel electrophoresis/mass spectrometry to study phosphorylated proteins or peptides, as they are often present in low abundance. Such proteins and peptides are of particular interest in proteomic studies, however, as signal transduction and other cellular processes are often regulated by phosphorylation/dephosphorylation cascades. In fact, approximately one-third of all proteins expressed by mammalian cells contain covalently bound phosphate groups.

One method currently in use for selectively enriching phosphorylated proteins in a sample involves β-elimination of the phosphate group from a phosphoserine or phosphothreonine amino acid residue to form an $\alpha,\beta$-unsaturated carbonyl. The $\alpha,\beta$-unsaturated carbonyl is a Michael acceptor and can react with a nucleophilic linker, such as ethanedithiol, which can be used to link the protein to a biotin affinity tag. Proteins having the biotin affinity tag are then selectively separated. However, this method suffers from the disadvantage that it cannot detect proteins that have phosphorylated tyrosine residues. In addition, a Michael reaction with a nucleophilic linker generates diastereoisomers which can complicate the analysis of the sample.

A second method for enriching the abundance of phosphorylated proteins in a sample involves selective immobilization of phosphorylated proteins on a metal-affinity column. Selectivity of this method is greatly increased when the carboxylic acid terminal of the proteins are esterified before sample is passed through the affinity column. However, since phosphorylated proteins are not covalently attached to the metal-affinity column, stringent washing conditions cannot be used to remove unwanted non-covalently associated molecules, such as cysteinyl peptides.

The above enrichment methods have greatly facilitated the study of phosphoproteomic. However, development of a phosphoprotein enrichment method that does not suffer from the disadvantages of the above methods would be desirable.

SUMMARY OF THE INVENTION

The present invention provides a system for separating phosphorylated peptides from a mixture of phosphorylated and unphosphorylated peptides. According to the invention, a collection of peptides, in which some of the peptides have one or more phosphate groups, is reacted with a first resin. In a particular embodiment, the peptides are first reacted with an amine protecting group, such as 2-(t-butoxycarbonyloxyimino)2-phenylacetonitrile (BOC-ON), thereby protecting the terminal amine group and other free amine groups on the peptides. In some embodiments, the first resin reacts with phosphate groups of the peptides, as well as with other groups that are present on both the phosphorylated peptides and the unphosphorylated peptides, such as the terminal carboxylic acid group, to form a bond. It is often desirable to selectively cleave any bonds that have formed between the first resin and a phosphate group of the phosphorylated peptides to regenerate the phosphate group so that a collection of peptides is formed in which the peptides are bound to the first resin and some of the peptides have one or more phosphate groups. In a one embodiment, the collection of peptides bound to the first resin is washed one or more times to remove unbound reagents.

According to the invention, the resin-reacted collection of peptides is reacted with a capture ligand to form a bond between the phosphorylated peptides and the capture ligand. In one embodiment, the capture ligand reacts with the phosphate group of phosphorylated peptides to form, for example, a phosphoramidate bond. In one embodiment, the capture ligand has different properties from the first resin, and these different properties allow peptides bound to the capture ligand to be separated from peptides that are not bound to the capture ligand. In another embodiment, the bond between the first resin and the peptides can be cleaved under conditions wherein the bond between the capture ligand and the peptides is stable so that a second collection of peptides is formed by selectively cleaving the first resin. This second collection of peptides comprises unphosphorylated peptides that are not bound to either the first resin or the capture ligand and phosphorylated peptides that are not bound to the first resin but are bound to the capture ligand.

In one embodiment, the capture ligand comprises a resin and the phosphorylated peptides that are bound to the capture ligand after cleavage of the first resin are separated from unphosphorylated peptides by filtration.

In another embodiment, the capture resin comprises a first recognition entity of a molecular recognition system that includes at least a first and a second recognition entities. In this embodiment, phosphorylated peptides that are bound to the first recognition entity are separated from unphosphorylated peptides, for example after cleavage of the first resin, by contacting a solution of the second collection of peptides with an affinity resin that comprises the second recognition entity of the molecular recognition system bound to a solid support. The first recognition entity binds to the second recognition entity, thereby binding the phosphorylated peptides to the affinity resin. The affinity resin may be washed one or more times to remove unbound peptides and reagents. The phosphorylated peptides are then released from the capture resin and collected separately, thereby separating phosphorylated peptides from unphosphorylated peptides. In one embodiment, the phosphorylated peptides are released from the capture resin by disrupting a bond between the first and the second recognition entity by, for example, contacting the resin with a solution having a high concentration of salt (e.g., at least about 0.1 M) or by contacting the resin with a solution having a different pH. Alternatively, the phosphorylated peptides can be released from the capture resin by cleaving a bond between the first recognition entity and the phosphorylated peptide. For example, when the bond between the phosphorylated peptides and the capture resin is a phosphoramidate bond, it can be cleaved by contacting the capture resin with an aqueous acid solution, such as an aqueous solution of trifluoroacetic acid. In a particular embodiment, the amine groups of the phosphorylated peptides have been protected with an acid labile amine protecting group, such as BOC-ON. In this embodiment, the amine protecting groups may be cleaved simultaneously with the bond between the first recognition entity and the phosphorylated peptide by, for example, contacting the capture resin with a concentrated solution of trifluoroacetic acid (e.g., 90% trifluoroacetic acid in 10% water). Alternatively, the phosphoramidate bond can be cleaved by contacting the capture resin with a weak basic solution, such as about a 2% aqueous diisopropyl ethyl amine solution.

In another aspect, the invention provides a kit for separating phosphorylated peptides from a mixture comprising phosphorylated peptides and unphosphorylated peptides according to the method of the invention. The kit comprises a first resin that can react with a carboxylic acid group of a peptide to form a covalent bond; and a capture ligand that can react with a phosphate group of a peptide to form a covalent bond. In one embodiment, the first resin provided in the kit can be cleaved from the peptide under conditions in which the bond between the capture ligand and the peptide is stable.

In another aspect, the invention provides a composition comprising a peptide bound to a capture ligand via a phosphoramidate bond. In a one embodiment, the peptide is also bound to a first resin that can be cleaved from the peptide under conditions wherein the bond between the capture ligand and the peptide are stable.

One particular advantage of the method of the invention is that it can be used to separate peptides that have phosphorylated tyrosine residues, as well as phosphorylated serine and threonine residues. Separation of the phosphorylated peptides from the unphosphorylated peptides allows less abundant phosphorylated peptides to be visualized by electrophoresis. Other advantages of the present invention are described further in the following detailed description of particular embodiments thereof.

BRIEF DESCRIPTION OF THE DRAWINGS

In FIGS. 1A and 1B, the shaded circles indicate first resin, the open circles indicate seiber amide resin and the dots indicate where a deuterium atom may be substituted for a hydrogen.

DETAILED DESCRIPTION OF CERTAIN EMBODIMENTS OF THE INVENTION

One interesting aspect of the study of proteomics is cellular regulation of signal transduction in response to intra- and extracellular stimuli. Protein kinases are involved in regulating signal transduction within a cell by phosphorylating serine, threonine and/or tyrosine amino acid residues of proteins. Thus, obtaining a phosphorylation profile of a cell under defined conditions can be useful in understanding cellular regulation of signal transduction. However, many phosphorylated proteins of interest are present in low abundance so that their presence is overwhelmed by other more abundant proteins and can go undetected by traditional methods of profiling cellular proteins.

The present invention provides a system for enriching phosphorylated peptides in a mixture of phosphorylated and unphosphorylated peptides. Once unphosphorylated peptides are removed from a sample, such as a biological sample, phosphorylated peptides that are present in low abundance are more readily detectable. The inventive system involves reacting a collection of peptides, in which some of the peptides have one or more phosphate groups, with a first resin. In one embodiment, the first resin will react with the carboxylic acid terminal of the peptides to form a bond. In one embodiment, the bond formed between the carboxylic acid terminal of the peptide and the first resin is a covalent bond, such as an amide bond or an ester bond. When the peptides are covalently bound to the first resin, they can be rigorously washed to remove noncovalently bound molecules, thereby improving the purity of the peptides. In one embodiment, the first resin has a plurality of primary or secondary amine groups and can react with the carboxylic acid terminal of the peptide to form an amide bond. In another embodiment, the resin has a plurality of hydroxy groups and can react with the carboxylic acid terminal of the peptide to form an ester bond. Typically, an amide or an ester bond is formed between the amine group or hydroxy group of the resin and the terminal carboxylic acid group of the peptide by using a coupling agent, such as diisopropylcarboximide (DIC), N-ethyl-N'-dimethylaminopropyl)-carbodiimide (EDC) or N,N'-dicyclohexyl-carbodiimide (DCC), which forms an O-acetyl isourea with the carboxylic acid terminal of the peptide which reacts rapidly with an amine group or hydroxy group on the resin to form an amide or an ester bond. The speed and yield of the coupling reaction may be improved by adding an alcohol that is substituted with an electron withdrawing group, such as hydroxybenzotriazole (HOBt) or p-nitrophenol, to the coupling reaction. The alcohol reacts with the O-acetyl isourea to form an active ester which then reacts with the amine group or hydroxy group of the resin to form an amide or an ester bond.

Figure 1A:
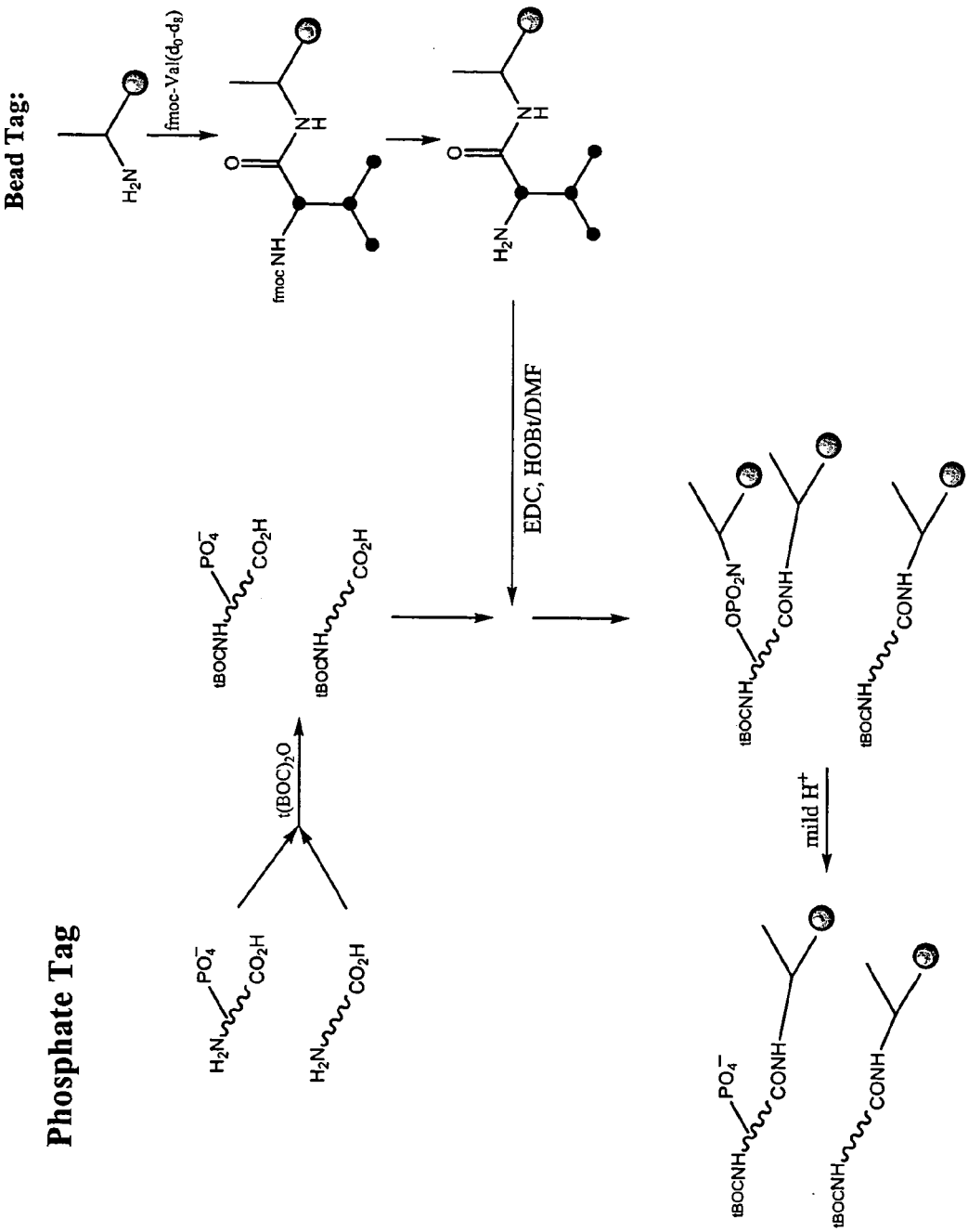
FIGS. 1A and 1B together are a schematic representation of reaction conditions for carrying out one embodiment of the method of the invention.
Figure 1B:
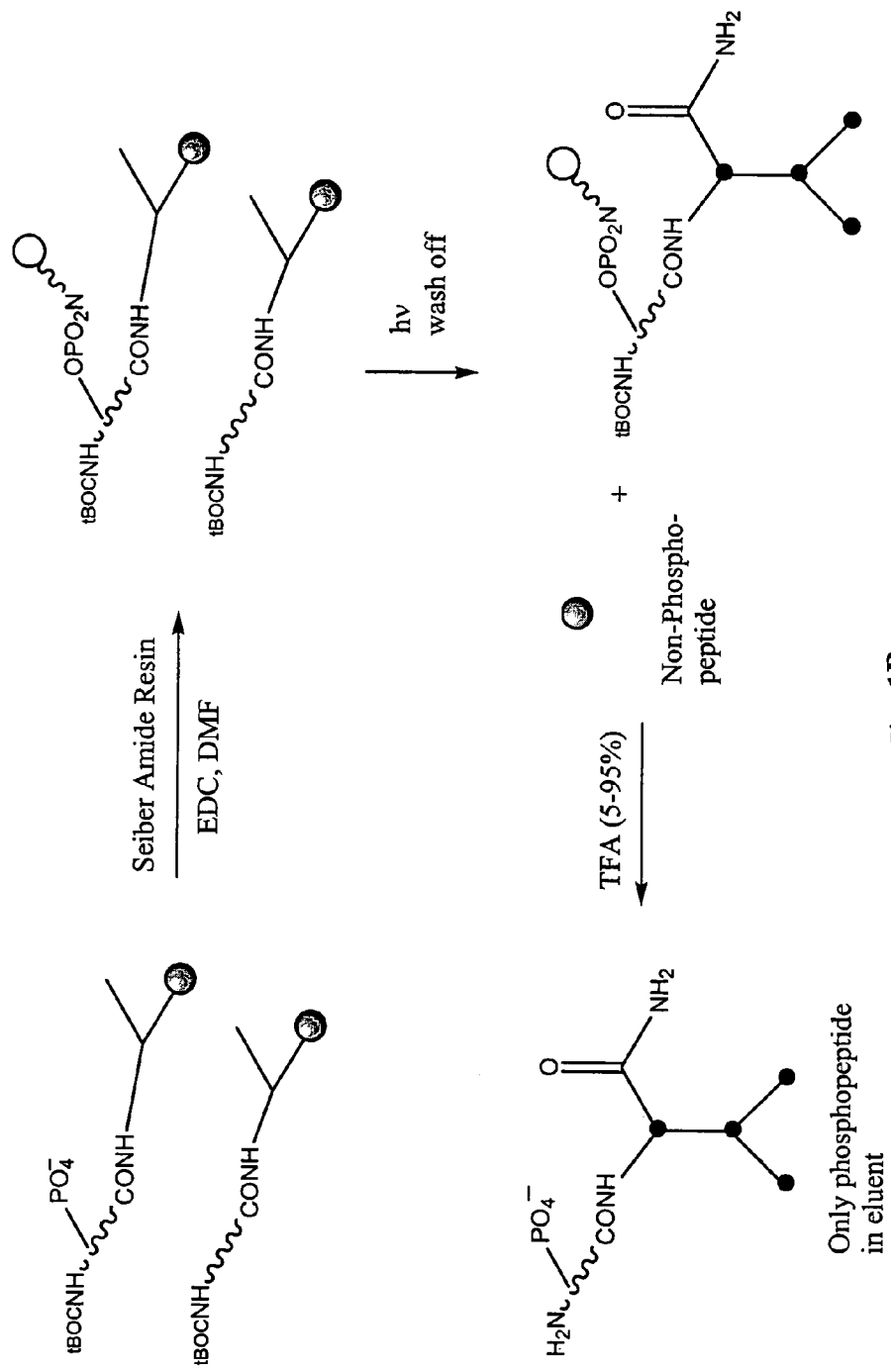

In another embodiment, a tagging group, such as a linker (e.g., dialkylamine, diaminoaryl, alkoxyalkylene, etc.), an amino acid or a peptide, that has a primary or secondary amine group, or a hydroxy group is bound to the first resin and can form an amide or ester bond with the carboxylic acid terminal of the peptides in the mixture of phosphorylated and unphosphorylated peptides. In some embodiments, the linker, amino acid or peptide that is bound to the resin can be labeled with an isotopically stable isotope by substituting an isotopically stable isotope, such as $^2$H, $^{13}$C, $^{15}$N, $^{17}$O, $^{18}$O, or $^{34}$S, for one of the atoms in the linker, amino acid or peptide (FIG. 1). In a particular embodiment, the tagging group is labeled with one or more deuterium ($^2$H). Typically, in this embodiment, after the peptides in the mixture have formed a bond with the resin bound tagging group, the tagging group, or a portion thereof, that was initially bound to the first resin will be transferred to the peptides from the peptide mixture when the first resin is cleaved and will remain bound thereto. For example, when a resin bound to an amino acid or a resin bound to a peptide is isotope labeled, the isotope label will be transferred to the carboxylic acid terminal of the phosphorylated and unphosphorylated peptides of the peptide mixture and thereby isotope labels the peptides in the mixture.

In some embodiments, the first resin reacts with phosphate groups of the peptides to form a bond. In this embodiment, it is generally desirable to selectively cleave any bonds that have formed between the first resin and a phosphate group of the phosphorylated peptides to regenerate the phosphate group, so that a collection of peptides is formed in which the peptides are bound to the first resin and some of the peptides have one or more phosphate groups. For example, when the first resin has a plurality of amine groups, some of the amine groups may react with phosphate groups of the peptide to form phosphoramidate bonds. Phosphoramidate bonds may be selectively cleaved without cleaving the amide bonds formed between the carboxylic acid terminal of the peptides and the first resin by contacting the resin bound peptides with a weak acid solution under mild conditions, such as 10% trifluoroacetic acid at room temperature.

The collection of peptides bound to the first resin is reacted with a capture ligand to form a bond between the phosphorylated peptides and the capture ligand. A "capture ligand," as used herein, is a recognition entity that is part of a recognition system or a resin. When the capture ligand is a resin, it can be bound directly to the phosphorylated peptides or may be bound to the phosphorylated peptides via a linker that is bound to the capture ligand and the phosphorylated peptide. For example, when the capture ligand has a primary or secondary amine group, it can react with the phosphate group of phosphorylated peptides to form a phosphoramidate bond. In one embodiment, the capture ligand will have different properties from the first resin that allow peptides bound to the capture ligand to be separated from peptides that are not bound to the capture ligand. For example, the capture ligand may be magnetic while the first resin is not magnetic. In one embodiment, a magnetic capture ligand includes elemental iron or an iron oxide. Magnetic particles suitable for use in the present invention are described in U.S. Pat. No. 6,551,843, the entire teachings of which are incorporated herein by reference.

Figure 2:
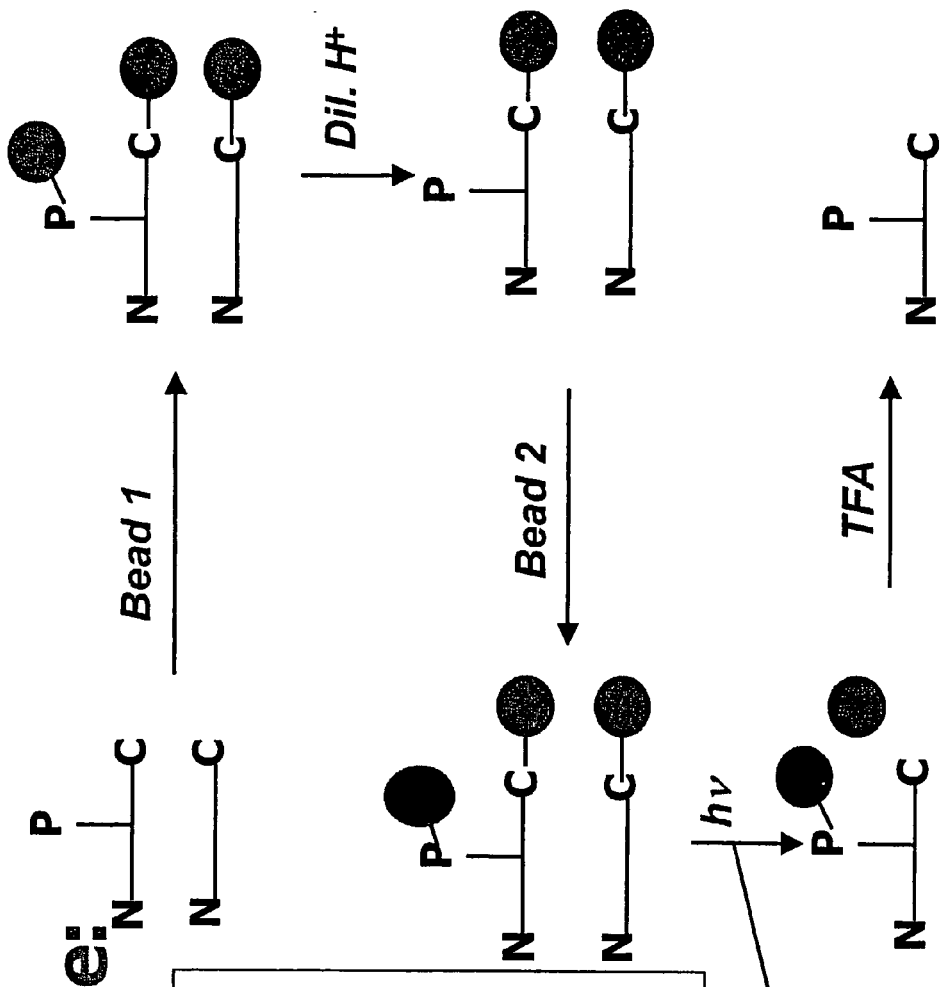
FIG. 2 is a schematic representation of one embodiment of the method of the invention that involves the use of a resin as a capture ligand.

In one embodiment, the first resin is selectively cleaved to form a second collection of peptides that comprises unphosphorylated peptides that are not bound to either the first resin or the capture ligand and phosphorylated peptides that are not bound to the first resin but are bound to the capture ligand. In one embodiment, the capture ligand is a second resin (FIG. 2) and the bond between the first resin and the peptides can be cleaved under conditions wherein the bond between the capture ligand and the peptides is stable. Phosphorylated peptides are separated from unphosphorylated peptides by filtering out the capture resin. In one embodiment, the peptides bound to the capture resin are washed one or more times with a solvent that will remove most of the unbound peptides and other reagents and impurities. Typically, about 60% or more of the unbound peptides are removed by the filtration and/or washing steps. In some instance, about 80%, about 90% or even about 100% of the unbound peptides are removed by the filtration and/or washing step. In a typical embodiment, at least about 75% of the phosphorylated peptides are recovered from the mixture of phosphorylated and unphosphorylated peptide. In some embodiments, recovery may be even higher, such as about 80%, about 85%, about 90%, about 95%, or about 100%.

In a one embodiment, the first resin is bound to the peptides by a photocleavable linker, and the capture ligand is bound to phosphorylated peptides by a bond that is not photocleavable, such as a phosphoramidate bond. In one embodiment, the photocleavable linker has structural formula I:

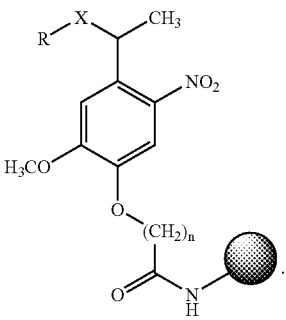

In structural formula I, n is an integer, typically from one to about 50, more typically, from one to about 20; X is —O— or —NH—; R is —H, an amino acid, a peptide, a linker, an isotope labeled amino acid, an isotope labeled peptide, or an isotope labeled linker; and the shaded circle represents a resin. When R is a peptide or an isotope labeled peptide, it typically has a length of between two amino acid residues to about 20 amino acid residues. When R is a linker, it can be, for example, an aminoalkyl, an aminoaryl, an isotopically labeled aminoalkyl, or an isotopically labeled aminoaryl. In one embodiment, when R is an aminoalkyl or an isotopically labeled aminoalkyl, it can be represented by the formula —$\{C(R^1)_2\}_m$—$NH_2$, and when R is an aminoaryl or an isotopically labeled aminoaryl it can be represented by the formula —$\{C_6(R^1)_4\}$—$NH_2$, wherein each $R^1$ is, independently, hydrogen or deuterium. The first resin is cleaved by exposing the resin bound peptides to light to form unphosphorylated peptides that are not bound to either the first resin or the capture ligand and phosphorylated peptides that are not bound to the first resin but are bound to the capture ligand.

The term "aliphatic," as used herein, means a straight chained or branched $C_1$–$C_{20}$ hydrocarbon or a cyclic $C_3$–$C_{20}$ hydrocarbon that is completely saturated or contains one or more unsaturated bonds but is not aromatic. The term "alkyl," as used herein, either alone or as part of another moiety (e.g., aminoalkyl, arylalkyl, etc.), means a straight chained or branched $C_1$–$C_{20}$ hydrocarbon or a cyclic $C_3$–$C_{20}$ hydrocarbon that is completely saturated. Aliphatic groups and alkyl groups may be substituted or unsubstituted.

An alkylene refers to an aliphatic group that has at least two points of attachment to at least two moieties (e.g., methylene, ethylene, isopropylene, etc.).

An alkyloxyalkylene refers to a group having the formula —O—{(alkylene) —O}$_q$—, wherein q is an integer from 1 to 10.

The term "aryl," as used herein, either alone or as part of another moiety (e.g., aminoaryl, arylalkyl, etc.), refers to carbocyclic aromatic groups such as phenyl. Aryl groups also include fused polycyclic aromatic ring systems in which a carbocyclic aromatic ring is fused to another carbocyclic aromatic ring (e.g., 1-naphthyl, 2-naphthyl, 1-anthracyl, 2-anthracyl, etc.) or in which a carbocyclic aromatic ring is fused to one or more carbocyclic non-aromatic rings (e.g., tetrahydronaphthylene, indan, etc.). The point of attachment of an aryl to a moiety may be on either the aromatic or non-aromatic ring. Aryl groups may be substituted or unsubstituted.

An arylene refers to an aryl group that has at least two points of attachment to at least two moieties (e.g., phenylene, etc.).

An arylalkyl group, as used herein, refers to an aryl group that is attached to another moiety via an alkylene linker.

The term "heteroaryl," as used herein, means an aromatic heterocycle which contains 1, 2, 3 or 4 heteroatoms selected from nitrogen, sulfur or oxygen. A heteroaryl may be fused to one or two rings, such as a cycloalkyl, a heterocycloalkyl, an aryl, or a heteroaryl. The point of attachment of a heteroaryl to a moiety may be on the heteroaryl, cycloalkyl, heterocycloalkyl or aryl ring, and the heteroaryl group may be attached through carbon or a heteroatom. Suitable heteroaryl groups include imidazolyl, furyl, pyrrolyl, thienyl, oxazolyl, thiazolyl, isoxazolyl, thiadiazolyl, oxadiazolyl, pyridinyl, pyrimidyl, pyrazinyl, pyridazinyl, quinolyl, isoquniolyl, indazolyl, benzoxazolyl, benzofuryl, benzothiazolyl, indolizinyl, imidazopyridinyl, pyrazolyl, triazolyl, isothiazolyl, oxazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo(b)thienyl each of which is optionally substituted. Heteroaryl groups may be substituted or unsubstituted.

A heterocycloalkyl refers to a non-aromatic ring which contains one or more oxygen, nitrogen or sulfur (e.g., morpholine, piperidine, piperazine, pyrrolidine, and thiomorpholine). Heterocycloalkyl groups may be substituted or unsubstituted.

A primary amine group has the formula —$NH_2$. A secondary amine group is a group having the formula —$NHR^2$, wherein $R^2$ is an aliphatic group or an aromatic group.

Suitable substituents for an aliphatic group, a heterocycloalkyl group, an aryl group, a heteroaryl group include any substituent that is stable under the reaction conditions used in the method of the invention. Examples of substituents for an aryl or a heteroaryl include an aryl (e.g., phenyl), an arylalkyl (e.g., benzyl), nitro, cyano, halo (e.g., fluorine, chlorine and bromine), alkyl (e.g., methyl, ethyl, isopropyl, cyclohexyl, etc.) haloalkyl (e.g., trifluoromethyl), alkoxy (e.g., methoxy, ethoxy, etc.), —$NR^3R^4$, —$NR^3C(O)R^5$, —$C(O)NR^3R^4$, —$C(O)R^3$, —$C(O)OR^3$, —$OC(O)R^5$, wherein $R^3$ and $R^4$ for each occurrence are, independently, —H, an alkyl, an aryl, or an arylalkyl; and $R^5$ for each occurrence is, independently, an alkyl, an aryl, or an arylalkyl.

Examples of suitable substituents for an aliphatic group or a heterocycloalkyl include the examples of substituents listed for aryl and heteroaryl groups as well as =O and =S.

In one embodiment, an aliphatic group, a heterocycloalkyl group, an aryl group, a heteroaryl group may include from one to about three substituents.

When a heterocycloalkyl or a heteroaryl group contain a nitrogen atom, it may be substituted or unsubstituted. When a nitrogen atom in the aromatic ring of a heteroaryl group has a substituent the nitrogen may be a quaternary nitrogen.

An alkoxy group refers to an aliphatic group attached to a molecule via an oxygen (i.e., —O-(aliphatic)).

An arylalkyl refers to an aryl group that is attached to a molecule via an alkyl group.

A haloalkyl group refers to an alkyl group that is substituted with one or more halogen atoms.

Figure 3:
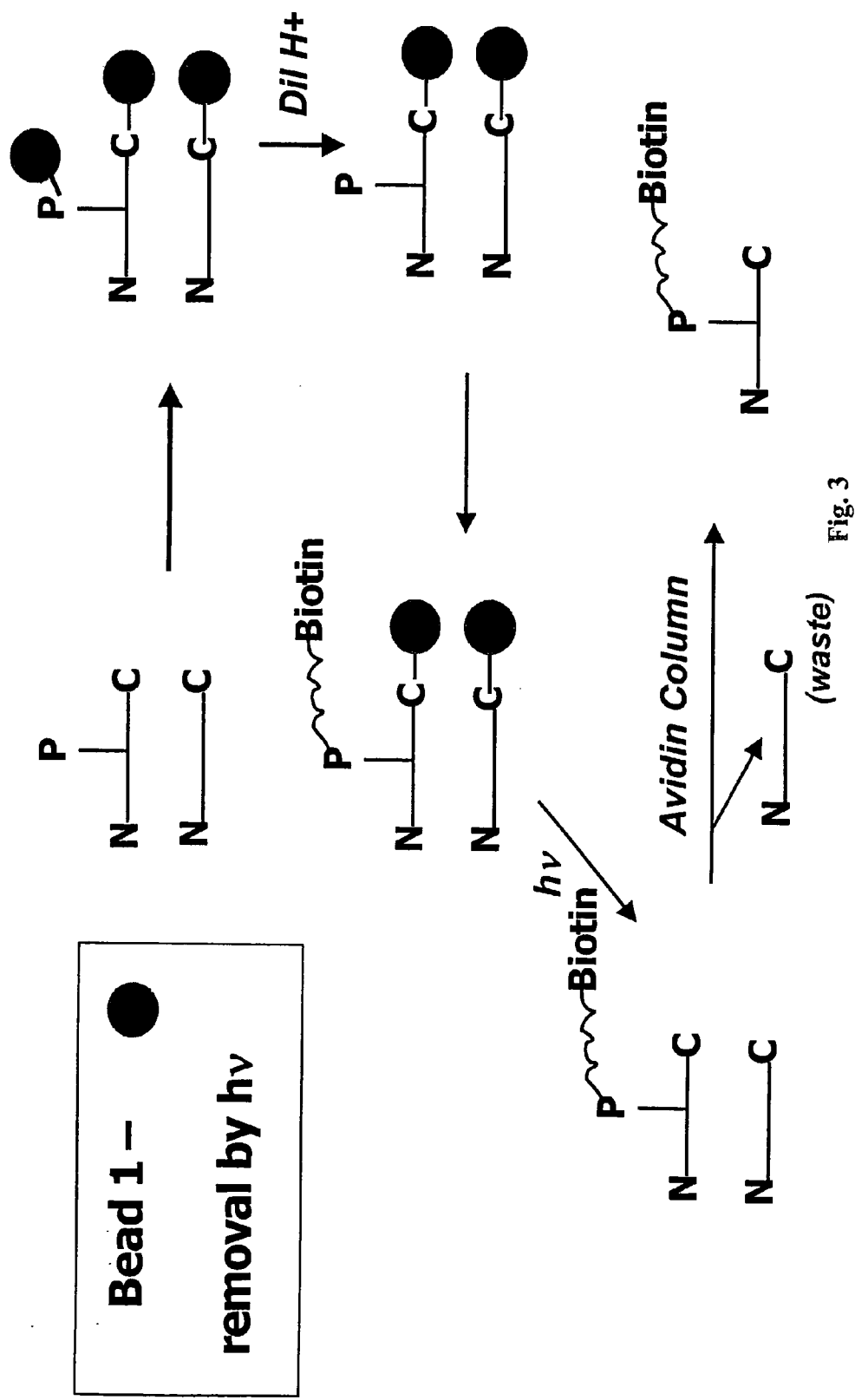
FIG. 3 is a schematic representation of one embodiment of the method of the invention that involves the use of a biotin as capture ligand.

In another embodiment, the capture ligand is a first recognition entity of a molecular recognition system (see FIG. 3). In this embodiment, phosphorylated peptides that are bound to the first recognition entity are separated from unphosphorylated peptides, for example after cleavage of the first resin, by contacting a solution of the second collection of peptides with an affinity resin that comprises a second recognition entity of the molecular recognition system bound to a solid support under conditions wherein the first and the second recognition entity can bind to each other. When the first and the second recognition entities bind to each other, the phosphorylated peptides become bound to the affinity resin. The affinity resin is then separated from the solution containing the second collection of peptides by, for example, filtration, thereby separating the phosphorylated peptides from unphosphorylated peptides. Optionally, the affinity resin may be washed one or more times to remove any unbound reagents or peptides. Typically, about 60% or more of the unbound peptides are removed by the filtration and/or washing steps. In some instances, about 80%, about 90% or even about 100% of the unbound peptides are removed by the filtration and/or washing step. In a typical embodiment, at least about 75% of the phosphorylated peptides are recovered from the mixture of phosphorylated and unphosphorylated peptide. In some embodiments, recovery may be even higher, such as about 80%, about 85%, about 90%, about 95%, or about 100%.

In one embodiment, the first resin is bound to the peptide by a photocleavable linker, such as the linker represented by formula I. In this embodiment, the first resin is cleaved by exposing the peptides to light to form a second collection of peptides in which unphosphorylated peptides are not bound to the first resin or the capture ligand, and phosphorylated peptides are not bound to first resin but are bound to the capture ligand.

Alternatively, phosphorylated peptides bound to a first recognition entity can be separated from unphosphorylated peptides by passing a solution of the second collection of peptides through a column comprising an affinity resin under condition wherein the first recognition entity can bind to the second recognition entity. An affinity resin is a resin that has a second recognition entity of a molecular recognition system bound to the resin.

A "molecular recognition system" is a system of at least two molecules or complexes which have a high capacity of molecular recognition for each other and a high capacity to specifically bind to each other. In a one embodiment, the binding is specific, and the capture ligand is part of a binding pair. Unless specified as a covalent bond, the term "bind" or "bound" includes both covalent and non-covalent associations. "Specific binding," as used herein, is when a recognition entity of a molecular recognition system binds one or more other molecule or complex, with specificity sufficient to differentiate between the molecule or complex and other components or contaminants of a sample. Molecular recognition systems for use in the invention are conventional and are not described here in detail. Techniques for preparing and utilizing such systems are well known in the art and are exemplified in the publication of Tijssen, P., "Laboratory Techniques in Biochemistry and Molecular Biology Practice and Theories of Enzyme Immunoassays" (1988), eds. Burdon and Knippenberg, New York: Elsevier, the entire teachings of which are incorporated herein. Examples of molecular recognition systems include an antigen/antibody, an antigen/antibody fragment, an avidin/biotin, a streptavidin/biotin, a protein A/$I_g$ or a lectin/carbohydrate.

Phosphorylated peptides can be released from the affinity resin by disrupting the bond or association between the first and the second recognition entities. In one embodiment, the association between the first and the second recognition entities is disrupted by washing the resin with a solution containing a high salt concentration (e.g., at least about 0.1 M salt). The peptides that are eluted in the high salt solution can be desalted and analyzed or the first recognition entity can be cleaved from the peptides before analysis. For example, when the first recognition entity is attached to the peptides via a phosphoramidate bond, the bond can be cleaved to regenerate a phosphate group by treating the peptides with an aqueous acid solution, such as trifluoroacetic acid (TFA) in water. Alternatively, the bond between the first recognition entity and the phosphorylated peptide can be cleaved while the peptides are attached to the column by incubating the column in an aqueous acid solution, such as TFA in water. The peptides can then be eluted from the column.

A phosphorylated peptide is a peptide that contains at least one phosphate group. Included in the term "phosphorylated peptides" are peptides in which a phosphate group has been converted into another group by forming a bond with a capture ligand or resin. For example, phosphorylated peptides include peptides that have formed a phosphoramidate bond with a capture ligand. An unphosphorylated peptide is a peptide that does not have a phosphate group or a phosphate group that has reacted with a capture ligand or resin to form a bond. In one embodiment, the peptides in a peptide sample are digested before binding to a resin or capture ligand. In this embodiment, phosphorylated or unphosphorylated peptides in the peptide sample have a molecular weight of about 5000 dalton or less after digestion.

A resin is a rigid or semirigid material, such as beads, pallets, disks, capillaries, hollow fibers, needles, membrane (e.g., porous membranes which allow fluid to flow therethrough), sheets, solid fibers, cellulose beads, pore-glass beads, silica gels, polystyrene beads optionally cross-linked with divinylbenzene, grafted co-polymer beads, poly-acrylamide beads, latex beads, dimethylacrylamide beads optionally cross-linked with N,N'-bis-acryloyl ethylene diamine, glass particles coated with a hydrophobic polymer, etc. In one embodiment, the resin is a non-biological polymer. As used herein, the term "non-biological polymer" includes inorganic polymers and organic polymers that can form bonds with a peptide directly or which can form a bond with a linker that has a group that can form a bond with a peptide. A linker is a group that is attached to a capture ligand or to the surface of a resin and can form a bond with at least one peptide. Examples of linkers include alkylenes, arylenes, alkoxyalkylenes, —$X_2$-(alkylene)-$X_3$—, —$X_2$-(arylene)-$X_3$—, —$X_2$-(alkylene)-(arylene)-$X_3$—, —$X_2$-(alkylene)-(arylene)-(alkylene)-$X_3$—, —{$X_2$-(alkylene)}$_p$-$X_3$—, and the like, wherein p is an integer from one to about ten; and $X_2$ and $X_3$ for each occurrence are, independently, —O—, —S—, or —$NR^2$—; and $R^2$ is an alkyl, aryl, or arylalkyl. In one embodiment, the linker is a photocleavable linker having, for example, the structural formula II:

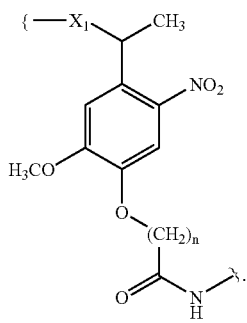

In structural formula II, n is as defined above, and $X_1$ is —O— or —NH—.

A suitable resin to use in the method of the invention is a resin that does not interfere with the process steps in the method of the invention and is stable to conditions used in the method of the invention. In one embodiment, the resin used in the method of the invention is a solid substrate composed of a homopolymer or a heteropolymer containing polystyrene, polyethylene, polyacrylamide, polyacrylein, polyethylene glycol, or the like. Suitable resins are available from a variety of commercial sources including Sigma-Aldrich, NovaBiochem, and Beckman-Coulter, or may be synthesized using known techniques. In one embodiment, the resin is magnetic, such as a magnetic particle. Magnetic particles suitable for use in the present invention are described in U.S. Pat. No. 6,551,843, the entire teachings of which are incorporated herein by reference.

In one embodiment, the amine groups of phosphorylated and unphosphorylated peptides in a peptide sample may be protected with an amine protecting group before attachment of the peptides to the first resin. The selection of a suitable amine protecting group depends upon the conditions to which the protecting group is being exposed and to other functional groups which may be present in the peptide molecule. Suitable amine protecting groups and reagents for protecting amines are described in Greene and Wuts, "Protective Groups in Organic Synthesis", John Wiley & Sons (1991), the entire teachings of which are incorporated into this application by reference. The skilled artisan can select, using no more than routine experimentation, suitable protecting groups for use in the disclosed method, including amine protecting groups other than those described below, as well as conditions for applying and removing the protecting groups to regenerate the amine group. Examples of suitable amine protecting groups include benzyloxycarbonyl, tert-butoxycarbonyl (BOC), tert-butyl, benzyl and fluorenylmethyloxycarbonyl (Fmoc).

An "amino acid" is compound represented by the formula $NR^1H$—$CHR^2COOH$, wherein $R^1$ is H and $R^2$ is H, an aliphatic group, a substituted aliphatic group, an aryl group, a substituted aryl group, a heteroaryl group or a substituted heteroaryl group; or $R^1$ and $R^2$, together form an alkylene connecting the amine group to the α-carbon (e.g., as in proline). An amino acid can react with other amino acids to form a peptide. Amino acid residues that form a peptide have the formula —$NR^1$—$CHR^2COO$— except for the amine terminal residue which has the formula $NR^1H$—$CHR^2COO$— and the carboxylic acid terminal residue which has the formula —$NR^1$—$CHR^2COOH$. A "naturally-occurring amino acid" is an amino acid found in nature. Examples include glycine, alanine, valine, leucine, isoleucine, aspartic acid, glutamic acid, serine, threonine, glutamine, asparagine, arginine, lysine, ornithine, proline, hydroxyproline, phenylalanine, tyrosine, tryptophan, cysteine, methionine and histidine. In one embodiment, when a resin has an amino acid residue or an isotope labeled amino acid residue bound thereto, it is a naturally occurring amino acid residue.

The invention also includes a kit for separating phosphorylated peptides from a mixture comprising phosphorylated peptides and unphosphorylated peptides. In one embodiment, the kit includes a first resin that can react with a carboxylic acid group of a peptide to form a covalent bond; and a capture ligand that can react with a phosphate group of a peptide to form a covalent bond. It is generally desirable that the bond formed between the first resin and the carboxylic acid group of the peptide can be cleaved under conditions in which the bond formed between the capture ligand and the peptide is stable.

In one embodiment, the kit also includes a reagent for protecting amine groups, such as BOC-ON, benzyloxycarbonyl chloride, benzyloxycarbonyl bromide, tert-butyl chloride, tert-butyl bromide, benzyl chloride, benzyl bromide, fluorenylmethyloxycarbonyl chloride, and fluorenylmethyloxycarbonyl bromide.

In another embodiment, the kit includes a reagent for cleaving the bond between the phosphate group of the peptide and the capture ligand to regenerate the phosphate group. For example, when the bond formed between the phosphate group of the peptide and the capture ligand is a phosphoramidate bond, the reagent used to cleave the bond and regenerate the phosphate group may be an aqueous acid solution, such as aqueous TFA.

In one embodiment, the kit includes a capture ligand that is a second resin. In another embodiment, the kit includes a capture ligand that comprises a first recognition entity. When the kit includes a capture ligand that comprises a first recognition entity, the kit may also include an affinity resin that comprises a second recognition entity bound to a solid support, wherein the first and the second recognition entity are part of a molecular recognition system.

In another embodiment, the kit includes a first resin that comprises an isotope labeled linker, an isotope labeled amino acid, or an isotope labeled peptide that can bind to peptides in the peptide mixture. When the peptides are cleaved from the first resin the isotope labeled linker, amino acid, or peptide remains bound to the peptides of the peptide mixture.

The invention is further illustrated by the following examples which are not intended to be limiting in any way.

EXAMPLES

I. Nitrogen Protection of Peptide Samples:

Peptide samples were placed into a 50:50 mixture of water and acetonitrile. Boc-ON (Aldrich # 19,337-2) was added at a 1.1 molar excess along with 1.6 molar excess of triethylamine as compared to the molar concentration of peptides in the sample. The reaction mixture became clear and was shaken at room temperature for 2.5–4 hr. The acetonitrile was removed in vacuo and the samples were dried down.

II. Attachment of Photo-Cleavable Resin (to Phosphate and Carboxylate Groups)

Fmoc-Aminoethyl Photolinker AM Resin (Calbiochem #01-64-0135) was prepared for coupling to peptide samples in the following way: At least an equimolar or greater amount of resin (0.6 mmol N/g) in relation to peptides present in the peptide sample was deprotected by placing the resin into a 20% solution of piperdine in anhydrous DMF. This was shaken at room temperature for 30 minutes. The resin was then filtered and rinsed with DMF. A combined solution of equimolar amounts of 1-hydroxybenzotriazole, peptide samples and diisopropylcarbodiimide (DIC) in a small amount of dry DMF was added to the deprotected resin in dry DMF. This mixture was shaken at room temperature for 90 min. The resin/beads were again filtered and washed with DMF, then methylene chloride. A final capping step was performed by placing the beads into methylene chloride containing 2 ml of 40% acetic anhydride/60% pyridine for 30 min. The resin was again filtered and washed with DMF.

II. Cleavage of Phosphoramidates and Biotin Attachment to Free Phosphates

The resin/beads from Step II were placed into a 10% TFA solution and shaken at room temperature overnight to cleave the weaker phosphoramidate bond. The resin was filtered and washed with DMF then re-suspended in DMF. A solution of equimolar amounts of 1-hydroxybenzotriazole, imino-biotin ethylenediamine amide-$d_0$/$d_4$ (prepared from ethylenediamine-$d_0$/$d_4$ and NHS-Iminobiotin trifluoroacetamide) and diisopropylcarbodiimide (DIC) in DMF were added to this resin. The mixture was shaken for 90 min at room temperature. Excess reagents were washed away when beads were again filtered off and washed with DMF.

IV. Cleavage of Resin

The beads were placed in shallow dish with 5 ml dioxane and allowed to swell. 10 μl ethanolamine was added as a scavenger. The dish was illuminated by a long-wave UV lamp (365 nm) for 3 hrs. The beads were filtered off and the filtrate was evaporated then placed onto the Avidin column.

V. Recovery of Phoshphate Enriched Peptide Samples

An Avidin column is equilibrated with 5 column volumes of 50 mM ammonium carbonate buffer containing 0.5 M NaCl, pH 11 (pH should be at 9.5 or higher for binding of biotin). The peptide samples are applied to the column and the column is washed with the ammonium carbonate buffer to remove any unbound (e.g., non-phosphorylated materials). The peptides are allowed to incubate for 30 minutes on the column, then the biotin-attached phosphorylated peptide samples are released by eluting the column with volumes of 50 mM ammonium acetate buffer containing 0.5 M NaCl, pH 4. These eluted samples may be desalted and treated with 90% TFA in water solution for 1.5 hr at 30 degrees to remove the N-terminal BOC-protecting groups and the biotin capture ligand.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method of separating phosphorylated peptides from a mixture comprising phosphorylated peptides and unphosphorylated peptides, comprising the steps of:
   a) reacting a collection of peptides with a non-magnetic first resin, wherein some of the peptides have one or more phosphate groups, wherein the first resin is a photocleavable resin represented by the following structural formula:

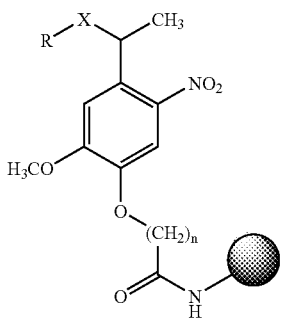

wherein, n is an integer,

X is —NH—,

R is —H, or an amino acid, a peptide, an isotope labeled amino acid, or an isotope labeled peptide with a primary or secondary amine, and shaded circle is a bead, a pallet, a disk, capillary, a hollow fiber, a needle, a membrane, a solid fiber, a cellulose bead, a polystyrene bead, a grafted co-polymer bead, a poly-acrylamide bead, a latex bead, a dimethylacrylamide bead, or combinations thereof;

wherein the primary or secondary amine groups represented by X and/or R react with the carboxylic acid groups of the peptides to form an amide bond and the phosphate groups of the peptides to form a phosphoramidate bond; thereby forming a first collection of peptides comprising unphosphorylated peptides with first resin bound carboxylic groups and phosphorylated peptides with first resin bound carboxylic acid and phosphate groups;

b) selectively cleaving the first resin that reacted with the phosphate groups of the phosphorylated peptides to regenerate the phosphate groups, thereby forming a second collection of peptides comprising unphosphorylated peptides with first resin bound carboxylic groups and phosphorylated peptides with first resin bound carboxylic acid groups;

c) reacting the phosphate groups of the second collection of peptides with a second resin to form a bond between the phosphorylated peptides and the second resin, wherein the second resin comprises an amino acid residue with a primary or secondary amine group, and wherein the second resin is magnetic, thereby forming a third collection of peptides comprising unphosphorylated peptides with first resin bound carboxylic groups and phosphorylated peptides with first resin bound carboxylic acid groups and second resin bound phosphate groups;

d) selectively cleaving the first resin by exposing the third collection of peptides to light, thereby forming a fourth collection of peptides comprising unphosphorylated peptides that are not bound to a resin and phosphorylated peptides that are bound to the second resin;

e) separating phosphorylated peptides from unphosphorylated peptides by exposing the fourth collection of peptides to a magnetic field and separating the peptides that are not bound to a resin from peptides that are bound to the second resin, thereby forming a fifth collection of peptide comprising phosphorylated peptides that are bound to the second resin.

2. The method of claim 1, further comprising the step of cleaving the bond between the second resin and the phosphorylated peptides in the fifth collection of peptides to form unbound phosphorylated peptides.

3. The method of claim 1, further comprising the step of reacting the peptides with a reagent for protecting amine groups before reacting the peptides with the first resin.

4. The method of claim 1, wherein the phosphoramidate bonds are selectively cleaved in step b) by contacting the first collection of peptides with a weak acid or a weak base.

5. The method of claim 1, wherein R is a peptide or an amino acid residue, wherein the peptide or amino acid residue has a primary or secondary amine group.

6. The method of claim 5, wherein the peptide or amino acid residue is isotope labeled, and wherein the isotope labeled peptide or amino acid residue remains bound to the peptide when the first resin is selectively cleaved.

7. A method of separating phosphorylated peptides from a mixture comprising phosphorylated peptides and unphosphorylated peptides, comprising the steps of:

a) reacting a collection of peptides with a non-magnetic first resin, wherein some of the peptides have one or more phosphate group, wherein the first resin is a photocleavable resin represented by the following structural formula:

wherein, n is an integer,

X is —NH—,

R is —H, or an amino acid, a peptide, an isotope labeled amino acid, or an isotope labeled peptide with a primary or secondary amine, and shaded circle is a bead, a pallet, a disk, capillary, a hollow fiber, a needle, a membrane, a solid fiber, a cellulose bead, a polystyrene bead, a grafted co-polymer bead, a poly-acrylamide bead, a latex bead, a dimethylacrylamide bead, or combinations thereof;

wherein the primary or secondary amine groups represented by X and/or R react with the carboxylic acid groups of the peptides to form an amide bond and the phosphate groups of the peptide to form a phosphoramidate bond; thereby forming a first collection of peptides comprising unphosphorylated peptides with first resin bound carboxylic groups and phosphorylated peptides with first resin bound carboxylic acid and phosphate groups;

b) selectively cleaving the first resin that reacted with the phosphate groups of the phosphorylated peptides to regenerate the phosphate groups, thereby forming a second collection of peptides comprising unphosphorylated peptides with first resin bound carboxylic groups and phosphorylated peptides with first resin bound carboxylic acid groups;

c) reacting the phosphate groups of the second collection of peptides with a capture ligand to form a bond between the phosphorylated peptides and the capture ligand, wherein the capture ligand is a first recognition entity of a molecular recognition system; thereby forming a third collection of peptides comprising unphosphorylated peptides with first resin bound carboxylic groups and phosphorylated peptides with first resin bound carboxylic acid groups and capture ligand bound phosphate groups;

d) selectively cleaving the first resin by exposing the third collection of peptides to light, thereby forming a fourth collection of peptides comprising unphosphorylated peptides that are not bound to a resin and phosphorylated peptides that are bound to the capture ligand;

e) separating peptides bound to the capture ligand from peptides that are not bound to the capture ligand, thereby separating phosphorylated peptides from unphosphorylated peptides.

8. The method of claim 7, further comprising contacting the fourth collection of peptides with an affinity resin, wherein the affinity resin comprises a second recognition entity of the molecular recognition system bound to a solid support, thereby binding the peptides bound to the first recognition entity to the affinity resin.

9. The method of claim 8, wherein the molecular recognition system comprises an antigen/antibody, an antigen/antibody fragment, an avidin/biotin, a streptavidin/biotin, a protein $A/I_g$ or a lectin/carbohydrate.

10. The method of claim 8, wherein the affinity resin is collected by filtration, thereby separating phosphorylated peptides from unphosphorylated peptides.

11. The method of claim 8, wherein the fourth collection of peptides is passed through a column comprising the affinity resin, thereby separating phosphorylated peptides from unphosphorylated peptides.

* * * * *